(12) United States Patent
Cozzi et al.

(10) Patent No.: US 6,458,768 B1
(45) Date of Patent: Oct. 1, 2002

(54) BENZOHETEROCYCLIC DISTAMYCIN DERIVATIVES, PROCESS FOR PREPARING THEM, AND THEIR USE AS ANTITUMOR AGENTS

(75) Inventors: Paolo Cozzi, Milan (IT); Pier Giovanni Baraldi, Ferrara (IT); Italo Beria, Villamarzana (IT); Marina Caldarelli, Milan (IT); Laura Capolongo, Milan (IT); Romeo Romagnoli, Ferrara (IT)

(73) Assignee: Pharmacia & Upjohn, S.p.A., Milan (IT)

( * ) Notice: Subject to any disclaimer, the term of this patent is extended or adjusted under 35 U.S.C. 154(b) by 0 days.

(21) Appl. No.: 09/623,505

(22) PCT Filed: Mar. 17, 1999

(86) PCT No.: PCT/EP99/01823

§ 371 (c)(1), (2), (4) Date: Sep. 19, 2000

(87) PCT Pub. No.: WO99/50266

PCT Pub. Date: Oct. 7, 1999

(30) Foreign Application Priority Data

Mar. 27, 1998 (GB) .................................................. 9806692

(51) Int. Cl.$^7$ ................................................. A61K 38/00
(52) U.S. Cl. ........................... 514/18; 514/14; 514/19; 514/408; 514/422
(58) Field of Search .......................... 514/17, 18, 19, 514/408, 422

(56) References Cited

U.S. PATENT DOCUMENTS 6,177,408 B1 * 1/2001 Cozzi et al. .................. 514/17

FOREIGN PATENT DOCUMENTS

| EP | 0 246 868 | 11/1987 | ......... C07D/207/34 |
|----|-----------|---------|----------------------|
| WO | 94 20463  | 9/1994  | ......... C07D/207/34 |
| WO | 96 05196  | 2/1996  | ......... C07D/403/14 |
| WO | 97 28123  | 8/1997  | ......... C07D/207/34 |
| WO | 98 21202  | 5/1998  | ......... C07D/403/14 |

* cited by examiner

Primary Examiner—James O. Wilson
Assistant Examiner—Patrick Lewis
(74) Attorney, Agent, or Firm—Arent Fox Plotkin Plotkin & Kahn, PLLC

(57) ABSTRACT

Compounds which are benzoheterocyclic distamycin derivatives of formula (I), wherein n is 2, 3 or 4; A is a heteroatom selected from O and S or is a group NR, wherein R is hydrogen or $C_1$–$C_4$ alkyl; B is CH or N; $R_1$ is hydrogen or $C_1$–$C_4$ alkyl; G is selected from the group consisting of (a, b, c, d, e, f, g, h, i, j), and —C≡N; wherein $R_5$, $R_6$, $R_7$, $R_8$, $R_9$, $R_{10}$, $R_{11}$ and $R_{12}$ are, independently from each other, hydrogen or $C_1$–$C_4$ alkyl; T is a group of formula (II) or (III) as defined above, wherein p is 0 or 1; $R_2$ and $R_3$ are, independently from each other, hydrogen, $C_1$–$C_4$ alkyl optionally substituted by one or more fluorine atoms, or $C_1$–$C_4$ alkoxy; $R_4$ is $C_1$–$C_4$ alkyl or $C_1$–$C_3$ haloalkyl; $X_1$ and $X_2$ are halogen atoms or pharmaceutically acceptable salts thereof; provided that at least one of $R_5$, $R_6$ and $R_7$ is alkyl; are useful as antitumor agents.

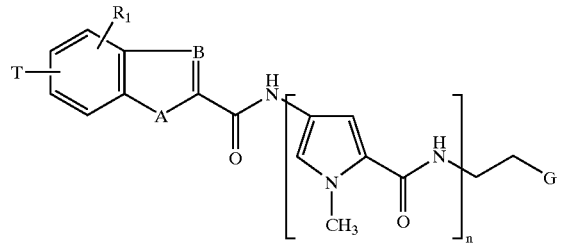

(I)

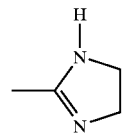

(a)

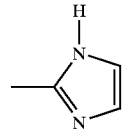

(b)

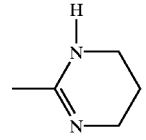

(c)

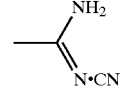

(d)

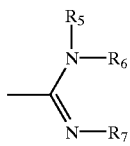

(e)

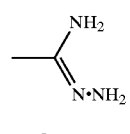

(f)

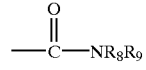

(g)

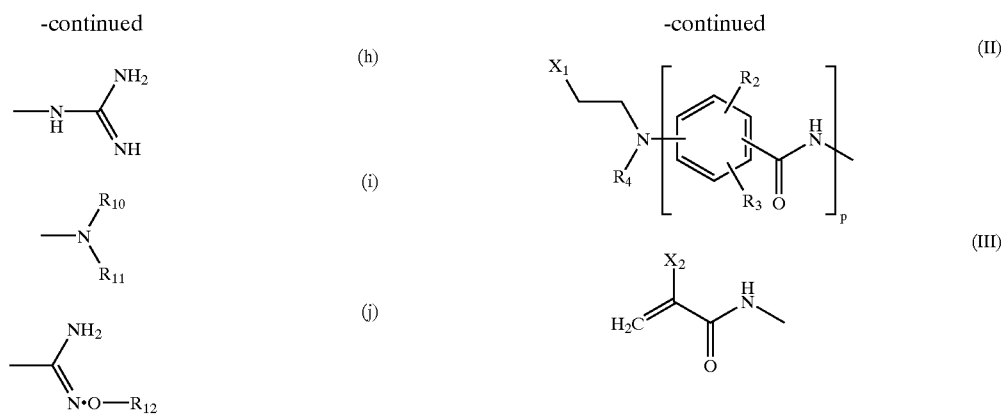
7 Claims, No Drawings

BENZOHETEROCYCLIC DISTAMYCIN DERIVATIVES, PROCESS FOR PREPARING THEM, AND THEIR USE AS ANTITUMOR AGENTS

The present invention relates to new alkylating antitumor agents analogous to Distamycin A, to a process for their preparation, to pharmaceutical compositions containing them and to their use as therapeutic agents. Distamycin A, whose formula is reported below,

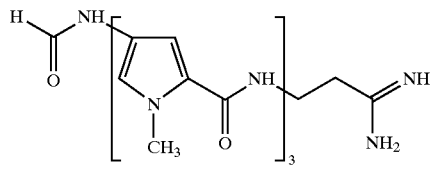

belongs to the family of the pyrroleamidine antibiotics and it is reported to interact reversibly and selectively with DNA-AT sequences, thus interfering with both replication and transcription. See, for a reference, Nature, 203, 1064 (1964); FEBS Letters, 7 (1970) 90; Prog. Nucleic Acids Res. Mol. Biol., 15, 285 (1975).

Several analogous to distamycin are known in the art. The international patent application WO 97/28123, in the name of the applicant, describes distamycin derivatives in which the distamycin formyl group is substituted by aromatic moieties bearing alkylating groups and the amidino moiety is replaced with other basic and non-basic nitrogen containing ending groups.

It has now been found that a new class of distamycin derivatives as defined hereinunder, wherein the distamycin formyl group is substituted by benzoheterocyclic rings bearing alkylating groups and the amidino moiety is substituted by different nitrogen-containing ending-groups, shows valuable biological properties.

Therefore, the present invention provides compounds which are distamycin derivatives of formula:

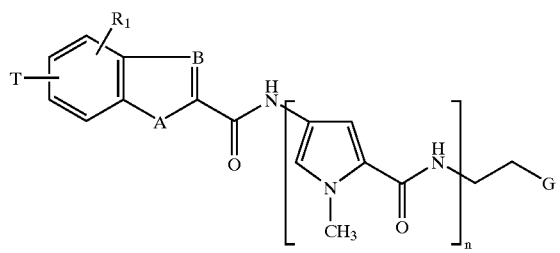

(I)

wherein:

n is 2, 3 or 4;

A is a heteroatom selected from O and S or is a group NR, wherein R is hydrogen or $C_1$–$C_4$ alkyl;

B is CH or N;

$R_1$ is hydrogen or $C_1$–$C_4$ alkyl;

G is selected from the group consisting of:

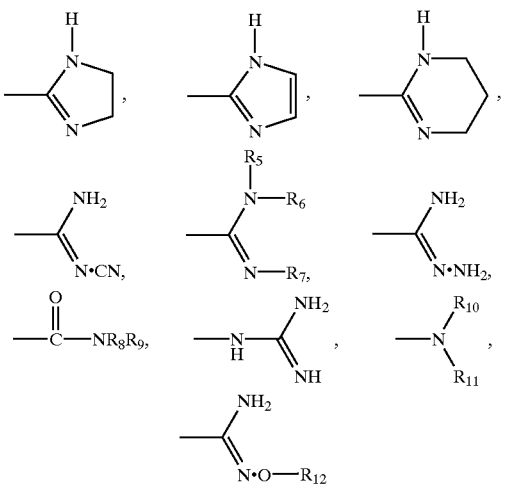

and —C≡N wherein $R_5$, $R_6$, $R_7$, $R_8$, $R_9$, $R_{10}$, $R_{11}$ and $R_{12}$ are, independently from each other, hydrogen or $C_1$–$C_4$ alkyl; T is a group of formula (II) or (III) as defined below

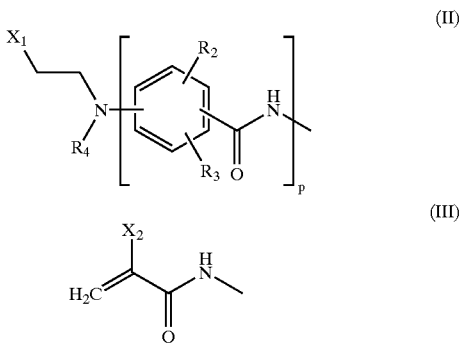

wherein p is 0 or 1; R and $R_3$ are, independently from each other, hydrogen, $C_1$–$C_4$ alkyl optionally substituted by one or more fluorine atoms, or $C_1$–$C_4$ alkoxy; $R_4$ is $C_1$–$C_4$ alkyl or $C_1$–$C_3$ haloalkyl; $X_1$ and $X_2$ are halogen atoms;

or a pharmaceutically acceptable salt thereof;

provided that at least one of $R_5$, $R_6$ and $R_7$ is alkyl.

The present invention includes within its scope also all the possible isomers covered by the compounds of formula (I), both separately and in admixture, as well as the metabolites and the pharmaceutically acceptable bio-precursors (otherwise known as pro-drugs) of the compounds of formula (I).

In the present description, unless otherwise specified, the term alkyl includes straight or branched alkyl, for instance $C_1$–$C_4$ alkyl such as methyl, ethyl, n-propyl, isopropyl, n-butyl, isobutyl, sec-butyl and tert-butyl; the term $C_1$–$C_4$ alkoxy includes straight or branched $C_1$–$C_4$ alkoxy such as methoxy, ethoxy, n-propoxy, isopropoxy, n-butoxy, isobutoxy, sec-butoxy and tert-butoxy.

Preferred $C_1$–$C_4$ alkyl or alkoxy groups are methyl, ethyl, propyl, methoxy and ethoxy groups.

The term $C_1$–$C_3$ haloalkyl embraces straight or branched $C_1$–$C_3$ alkyl substituted by one or more halogen atoms; the term halogen atom includes fluorine, chlorine, bromine and iodine.

Preferred halogen atoms are chlorine or bromine whilst preferred $C_1$–$C_3$ haloalkyl groups are 2-chloroethyl or 2-bromoethyl. When substituted by fluorine atoms, the $C_1$–$C_4$ alkyl groups are preferably $C_1$–$C_4$ perfluoroalkyl groups, i.e. trifluoromethyl.

Within the compounds of formula (I) wherein T is a group of formula (II) as defined above and p is 1, the carboxamido and amino groups onto phenyl ring are in ortho, meta or para position with respect to each other; preferably the carboxamido and the amino groups are in meta or para position.

Pharmaceutically acceptable salts of the compounds of formula (I) are their salts with pharmaceutically acceptable either inorganic or organic acids such as, for instance, hydrochloric, hydrobromic, sulfuric, nitric, acetic, propionic, succinic, malonic, citric, tartaric, methanesulfonic and p-toluenesulfonic acid.

A preferred class of compounds of the present invention is that wherein, in formula (I):
n is 2 or 3;
A is O, S, NH or $NCH_3$;
$R_1$ is hydrogen;
G is selected from:

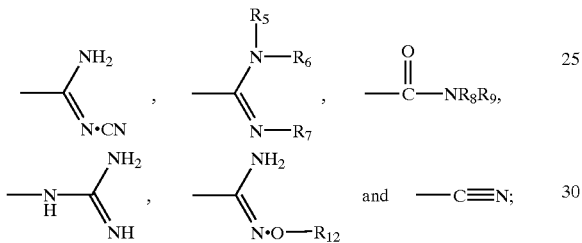

wherein $R_5$, $R_6$, and $R_7$ are, independently from each other, hydrogen or methyl; $R_8$, $R_9$ and $R_{12}$ are hydrogen; T is a group of formula (II) as above wherein p is 0, $X_1$ is a chlorine atom and $R_4$ is 2-chloroethyl or T is a group of formula (III) as above wherein $X_2$ is chlorine or bromine. Examples of specific compounds according to the present invention, especially in the form of salts, preferably with hydrochloric acid, are the following:

1) 3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propioncyanamidine;
2) 3-[1-methyl-4[1-methyl-4[1-methyl-4[1-methyl-5(α-bromoacrylamido)indazole-2-carboxamido]pyrrole-2-carboxamido]pyrrole-2-carboxamido]pyrrole-2-carboxamido]propioncyanamidine;
3) 3-[1-methyl-4[1-methyl-4[1-methyl-4[5(α-bromoacrylamido)indole-2-carboxamido]pyrrole-2-carboxamido]pyrrole-2-carboxamido]propion-N-methylamidine;
4) 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propion-N-methylamidine;
5) 3-[1-methyl-4[1-methyl-4[1-methyl-4[1-methyl-5(α-chloroacrylamido)indole-2-carboxamido]pyrrole-2-carboxamido]pyrrole-2-carboxamido]pyrrole-2-carboxamido]propion-N-methylamidine;
6) 3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propion-N-methylamidine;
7) 3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propion-N-methylamidine;
8) 3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propion-N,N'-dimethylamidine;
9) 3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propion-N,N'-dimethylamidine;
10) 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propion-N,N'-dimethylamidine;
11) 3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propion-N,N'-dimethylamidine;
12) 3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propion-N,N'-dimethylamidine;
13) 3-[1-methyl-4[1-methyl-4[1-methyl-4[1-methyl-5(α-bromoacrylamido)indazole-2-carboxamido]pyrrole-2-carboxamido]pyrrole-2-carboxamido]pyrrole-2-carboxamido]propion-N,N'-dimethylamidine;
14) 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamidoxime;
15) 3-[1-methyl-4[1-methyl-4[1-methyl-4[5(α-bromoacrylamido)indazole-2-carboxamido]pyrrole-2-carboxamido]pyrrole-2-carboxamido]pyrrole-2-carboxamido]propionamidoxime;
16) 3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propionamide;
17) 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamide;
18) 3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propionamide;
19) 3-[1-methyl-4[1-methyl-4[1-methyl-4[1-methyl-5(α-chloroacrylamido)indazole-2-carboxamido]pyrrole-2-carboxamido]pyrrole-2-carboxamido]pyrrole-2-carboxamido]propionamide;
20) 2-[1-methyl-4[1-methyl-4[1-methyl-4[5(α-bromoacrylamido)benzofurane-2-carboxamido]pyrrole- 2-carboxamido]pyrrole-2-carboxamido]pyrrole-2-carboxamido]ethylguanidine;
21) 2-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]ethylguanidine;
22) 3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propionitrile;
23) 3-[1-methyl-4[1-methyl-4[1-methyl-4[1-methyl-5(α-bromoacrylamido)indole-2-carboxamido]

pyrrole-2-carboxamido]pyrrole-2-carboxamido]
pyrrole-2-carboxamido]propionitrile;
24) 3-[1-methyl-4[1-methyl-4[1-methyl-4[5-N,N-bis (2-chloroethyl)aminobenzofurane-2-carboxamido] pyrrole-2-carboxamido]pyrrole-2-carboxamido] pyrrole-2-carboxamido]propioncyanamidine;
25) 3-[1-methyl-4[1-methyl-4[1-methyl-4[5-N,N-bis (2-chloroethyl)aminoindazole-2-carboxamido] pyrrole-2-carboxamido]pyrrole-2-carboxamido] pyrrole-2-carboxamido]propion-N-methylamidine;
26) 3-[1-methyl-4[1-methyl-4[1-methyl-4[1-methyl-5-N,N-bis(2-chloroethyl)aminoindazole-2-carboxamido]pyrrole-2-carboxamido]pyrrole-2-carboxamido]pyrrole-2-carboxamido]propion-N,N'-dimethylamidine;
27) 3-[1-methyl-4-[1-methyl-4-[1-methyl-4-[5-N,N-bis(2-chloroethyl)aminoindole-2-carboxamido] pyrrole-2-carboxamido]pyrrole-2-carboxamido] pyrrole-2-carboxamido]propionamidoxime;
28) 3-[1-methyl-4[1-methyl-4[1-methyl-4[5-N,N-bis (2-chloroethyl)aminobenzofurane-2-carboxamido] pyrrole-2-carboxamido]pyrrole-2-carboxamido] pyrrole-2-carboxamido]propionamidoxime;
29) 3-[1-methyl-4[1-methyl-4[1-methyl-4[5-N,N-bis (2-chloroethyl)aminobenzothiophene-2-carboxamido]pyrrole- 2-carboxamido]pyrrole-2-carboxamido]pyrrole-2-carboxamido]propionamide;
30) 2-[1-methyl-4[1-methyl-4[1-methyl-4[5-N,N-bis (2-chloroethyl)aminoindole-2-carboxamido]pyrrole-2-carboxamido]pyrrole-2-carboxamido]pyrrole-2-carboxamido]ethylguanidine;
31) 2-[1-methyl-4[1-methyl-4[1-methyl-4[1-methyl-5-N,N-bis(2-chloroethyl)aminoindole-2-carboxamido] pyrrole-2-carboxamido]pyrrole-2-carboxamido] pyrrole-2-carboxamido]ethylguanidine;
32) 3-[1-methyl-4[1-methyl-4[1-methyl-4[5-N,N-bis (2-chloroethyl)aminoindazole-2-carboxamido] pyrrole-2-carboxamido]pyrrole-2-carboxamido] pyrrole-2-carboxamido]propionitrile.

A further object of the present invention is a process for preparing the compounds of formula (I), and the pharmaceutically acceptable salts thereof, which process comprises:

(a) reacting a compound of formula:

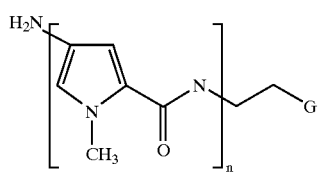

(IV)

wherein n and G are as defined above; with a compound of formula:

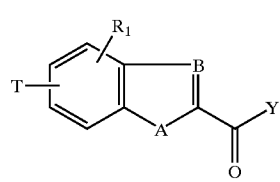

(V)

wherein A, B, T and $R_1$ are as defined above; is hydroxy or a suitable leaving group; to obtain a compound of formula (I) as defined above; or (b) reacting a compound of formula:

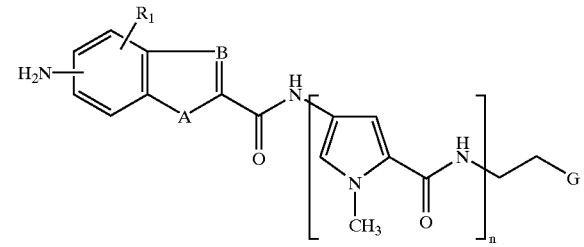

(VI)

wherein n, A, B, G and $R_1$ are as defined above; with a compound of formula:

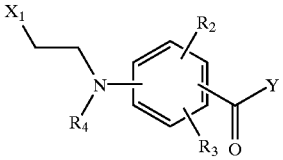

(VIIa)

wherein $X_1$, $R_2$, $R_3$, $R_4$ and Y are as defined above; or, alternatively, with a compound of formula:

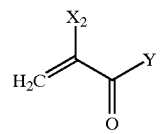

(VIIb)

wherein $X_2$ and Y are as defined above; to obtain a compound of formula (I) wherein T is a group of formula (II) with p equal to 1 or a group of formula (III); or (c) reacting a compound of formula (VIII)

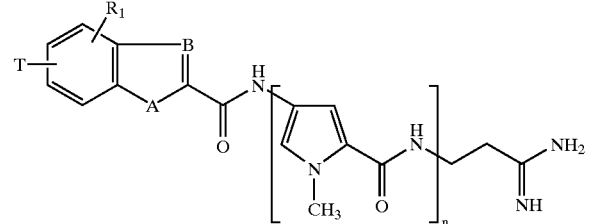

(VIII)

wherein n, A, B, $R_1$ and T are as defined above; with succinic anhydride, so obtaining a compound of formula (I) having G equal to —C≡N; or (d) reacting a compound of formula (IX):

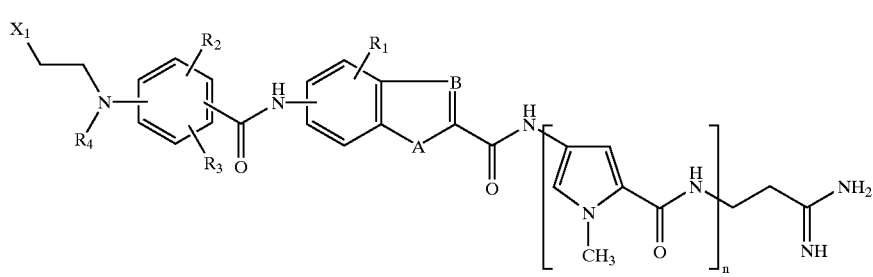

wherein n, A, B, $R_1$, $R_2$, $R_3$, $R_4$ and $X_1$ are as defined above; with (i) $H_2N—(CH_2)_m—NH_2$, where m is 2 or 3, to obtain a compound of formula (I) wherein G is:

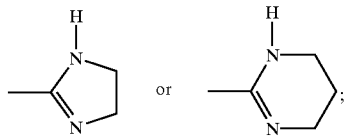

(ii) $H_2N—CH_2—CHO$ to obtain a compound of formula (I) wherein G is:

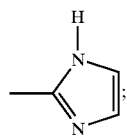

(iii) $H_2N—CN$, so obtaining a compound of formula (I) having G equal to:

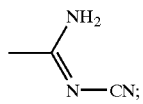

(iv) $H_2N—OR_{12}$, wherein $R_{12}$ is as defined above, so obtaining a compound of formula (I) having G equal to:

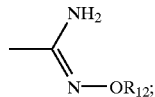

(v) $H_2N—NH_2$, so obtaining a compound of formula (I) having G equal to:

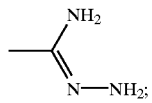

(vi) $HNR_5R_6$, so obtaining a compound of formula (I) having G equal to:

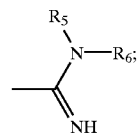

and then optionally with $H_2NR_7$, so obtaining a compound of formula (I) having G equal to:

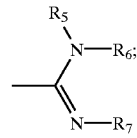

wherein $R_5$, $R_6$, and $R_7$ are, independently from each other, hydrogen or $C_1$–$C_4$ alkyl;

(vii) $HNR_8R_9$, so obtaining a compound of formula (I) having G equal to:

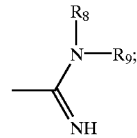

and then with water in an alkaline medium, so obtaining a compound of formula (I) having G equal to —CO—$NR_8R_9$, wherein $R_8$ and $R_9$ are, independently from each other, hydrogen or $C_1$–$C_4$ alkyl; or (viii) water in an alkaline medium, so obtaining a compound of formula (I) having G equal to —$CONH_2$;

and, if desired, (e) converting a compound of formula (I) into a pharmaceutically acceptable salt thereof.

In the compounds of formula (V), (VIIa) and (VIIb), Y is hydroxy or a suitable leaving group such as, for instance, chloro, 2,4,5-trichlorophenoxy, 2,4-dinitrophenoxy, succinimido-N-oxy, imidazolyl group, and the like.

The condensation reactions as set forth above under processes (a) and (b) can be carried out according to known methods, for instance those described in EP-A-246,868 and in the aforementioned WO 97/28123.

The reaction of a compound of formula (IV) with a compound of formula (V) wherein Y is hydroxy is preferably carried out with a molar ratio (IV):(V) of from 1:1 to 1:2, in an organic solvent such as, e.g., dimethylsulphoxide, dimethylacetamide, dimethylformamide, ethanol, benzene, or pyridine, in the presence of an organic or inorganic base such as, e.g., triethylamine, N,N'-diisopropylethylamine, or sodium or potassium carbonate or bicarbonate, and a condensing agent such as, e.g., N-ethyl-N'-(3-dimethylaminopropyl)carbodiimide, N,N'-dicyclohexylcarbodiimide, or 1-hydroxybenzotriazole hydrate. The reaction temperature may vary from about −10° C. to about 100° C., and the reaction time from about 1 to about 24 hours.

The reaction between a compound of formula (IV) and a compound of formula (V) wherein Y is a leaving group as defined above, may be carried out with a molar ratio (IV):(V) of from about 1:1 to about 1:2, in an organic solvent such as, e.g., dimethylformamide, dioxane, pyridine, tetrahydrofuran, or mixtures thereof with water, optionally in the presence of an organic base, e.g. N,N'-diisopropylethylamine, triethylamine, or an inorganic base, e.g. sodium or potassium bicarbonate, at a temperature of from about 0° C. to about 100° C., and for a time varying from about 2 hours to about 48 hours.

The compounds of formula (IV) are known compounds, or may be prepared by known methods, for instance as described in WO 97/28123.

The compounds of formula (V) wherein Y is hydroxy and T is a group of formula (II) with p equal to 1, or a group of formula (III), can be prepared by reacting an amino compound of formula:

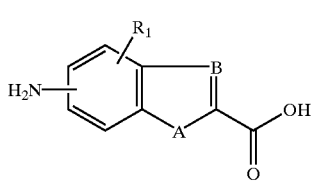

wherein A, B and $R_1$ are as defined above, with a compound of formula (VIIa) or (VIIb) as defined above.

The compounds of formula (V) wherein Y is hydroxy and T is a group of formula (II) with p equal to 0, can be prepared by reacting a compound of formula:

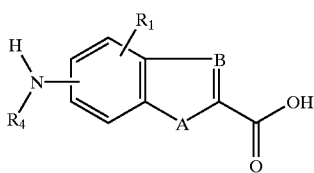

wherein A, B, $R_1$, and $R_4$ are as defined above, with ethylene oxide and then with a halogenating agent. Before carrying out the reaction, the carboxyl group is preferably protected with a suitable protecting group according to known techniques.

The compounds of formula (V) wherein Y is a leaving group can be prepared starting from the corresponding acids through well known reactions.

The compounds of formula (X) and (XI) are commercial products, or can be obtained by known methods. See, for a reference, J. Am. Chem. Soc. 80, 4621 (1958); Helv. Chim. Acta 31, 75 (1948); Synth. Commun. 21, 959 (1991); Anti-cancer Drug Design 10, 25 (1995); J. Org. Chem. 26, 4996–97 (1961); or Synth. Commun. 24, 3129–3134 (1994).

The carboxylic acids of formula (VIIa) and (VIIb), or the derivatives thereof, are commercially available products, or may be prepared through reactions well known in organic chemistry. See, for a reference, Tetrahedron Letters 31 1299 (1990); Anti-cancer Drug Design 9, 511 (1994); JACS 62 3495 (1940); J.Org. Chem. 26 4996–97 (1961); or Synth. Commun. 24 3129–3134 (1994).

The compounds of formula (VI) can be obtained by nitro-group reduction, according to known methods, of the compounds of formula:

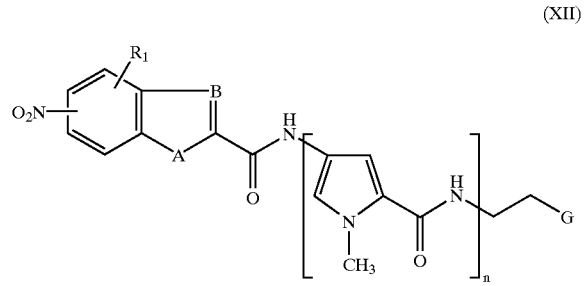

wherein n, A, B, $R_1$ and G are as defined above.

In their turn, the nitro-derivatives of formula (XII) can be obtained by reacting a compound of formula (IV) as defined above with a compound of formula:

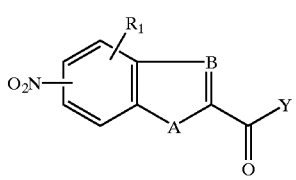

wherein A, B, $R_1$ and Y are as defined above.

The compounds of formula (XIII) are known compounds, or may be obtained by known methods. See, for a reference, Tetrahedron Letters 31, 1299 (1990); Anti-cancer Drug Design 9, 511 (1994); JACS 62, 3495 (1940); J. Org. Chem. 26, 4996–97 (1963); or Synth. Commun. 24, 3129–3134 (1994). The reaction according to process (c) can be carried out analogously to what described in U.S. Pat. No. 4,738,980. The halogenating agent may be, e.g., an elemental halide, such as chlorine or bromine, or a thionyl halide, such as thionylchloride.

The reaction of a compound of formula (VIII) with succinic anhydride is preferably carried out with a molar ratio (VIII):succinic anhydride of from 1:1 to 1:3 in an organic solvent such as, e.g., dimethylsulphoxide, in the presence of an organic or inorganic base such as, for instance, diisopropylethylamine, triethylamine, sodium or potassium carbonate and the like.

The reaction temperature may vary from about 25° C. to about 100° C., and for a time varying from about 1 hour to about 12 hours.

The compounds of formula (VIII) are known compounds or can be prepared from known compounds through well known reactions in organic chemistry as described, for instance, in J. Med. Chem. 9, 882, (1996); J. Med. Chem. 25, 178, (1982); J. Org. Chem. 26, 4996, (1961); J. Heterocyclic Chem. 32, 1063, (1995); or Synth. Commun. 24, 3129–3134, (1994).

The reaction between a compound of formula (IX) and one of the reactants as described in points (i–vi) according to process (d), can be carried out according to known methods, for instance those described in U.S. Pat. No. 4,766,142; Chem. revs. (1961), 155; J. Med. Chem. (1984), 27, 849–857; Chem. Revs. (1970), 151; and "The Chemistry of amidines and imidates", edited by S. Patai, John Wiley & Sons, N.Y. (1994).

The reaction in water in an alkaline medium as set forth in points (vii–viii) may be carried out according to known methods usually employed for alkaline hydrolysis, e.g. by treating the substrate with an excess of sodium or potassium hydroxide dissolved in water or into a water/organic solvent admixture, e.g. dioxane, tetrahydrofuran or acetonitrile at a temperature of from 50° C. to about 100° C., for a time varying from about 2 hours to about 48 hours.

In view of what above reported, it is clear to the man skilled in the art that when preparing the compounds of formula (I) according to processes (a)–(d) as set forth above, optional amino groups, i.e. $R_{10}$ and/or $R_{11}$ of the compounds of formula (IV) and (VI) equal to hydrogen, need to be properly protected according to conventional techniques, so as to avoid unwanted side reactions.

Likewise, the conversion of the said protected amino groups into the free amines may be carried out according to known procedures. See, for a general reference, J. Org. Chem. 43, 2285, (1978); J. Org. Chem. 44, 811 (1979); J. Am. Chem. Soc. 78, 1359 (1956); Ber. 65, 1192 (1932); and J. Am Chem. Soc. 80, 1154, (1958).

Salification of a compound of formula (I), as well as preparation of a free compound starting from a salt, may be carried out by known standard methods. Well known procedures such as, e.g., fractional crystallisation or chromatography, may also be followed for separating a mixture of isomers of formula (I) into the single isomers.

The compounds of formula (I) may be purified by conventional techniques such as, e.g., silica gel or alumina column chromatography, and/or by recrystallisation from an organic solvent such as, e.g., a lower aliphatic alcohol, e.g. methyl, ethyl or isopropyl alcohol, or dimethylformamide.

Pharmacology

The compounds of formula (I) according to the present invention are useful as antineoplastic agents. Particularly, they show cytostatic properties towards tumor cells, so that they can be useful to inhibit growth of various tumors in mammals, including humans, such as, for instance, carcinomas, e.g. mammary carcinoma, lung carcinoma, bladder carcinoma, colon carcinoma, ovary and endometrial tumors. Other neoplasias in which the compounds of the present invention can find application are, for instance, sarcomas, e.g. soft tissue and bone sarcomas, and the hematological malignancies such as, e.g. leukemias.

The in vitro antitumor activity of the compounds of formula (I) was evaluated by cytotoxicity studies carried out on murine $L_{1210}$ leukemia cells. Cells were derived from in vivo tumors and established in cell culture. Cells were used until the tenth passage. Cytotoxicity was determined by counting surviving cells after 48 hours treatment.

The percentage of cell growth in the treated cultures was compared with that of controls. $IC_{50}$ values (concentration inhibiting 50% of the cellular growth in respect to controls) were calculated on dose-response.

The compounds of the invention were tested also in vivo on $L_{1210}$ murine leukemia and on murine reticulosarcoma M 5076, showing a very good antitumoral activity, with the following procedure.

$L_{1210}$ murine leukemia was maintained in vivo by i.v. serial transplantation. For experiments, $10^5$ cells were injected i.p. in CD2F1 female mice, obtained from Charles River Italy. Animals were 8 to 10 weeks old at the beginning of the experiments. Compounds were administered i.v. at day +1 after tumor cells injections.

M5076 reticulosarcoma was maintained in vivo by i.m. serial transplantation. For experiments, $5 \times 10^5$ cells were injected i.m. in C57B16 female mice, obtained from Charles River Italy. Animals were 8 to 10 weeks old at the beginning of the experiments. Compounds were administered i.v. at day 3, 7 and 11 after tumor injection.

Survival time of mice and tumor growth were calculated and activity was expressed in term of T/C% and T.I.%.

$$T/C = \frac{\text{median survival time treated group}}{\text{median survival time untreated group}} \times 100$$

T.I.=% inhibition of tumor growth respect to control
Tox=number of mice which died for toxicity.

Tox determination was made when mice died before the control and/or tested significant body weight loss and/or spleen and/or liver size reduction were observed.

The compounds of the invention can be administered to mammals, including humans, through the usual routes, for example, parenterally, e.g. by intravenous injection or infusion, intramuscularly, subcutaneously, topically or orally. The dosage depends on age, weight and conditions of the patient and on the administration route. For example, a suitable dosage for administration to adult humans may range from about 0.1 to about 150–200 mg pro dose 1–4 times a day.

Further object of the present invention are pharmaceutical compositions, which comprise a compound of formula (I) as an active principle, in association with one or more pharmaceutically acceptable carrier and/or diluent.

The pharmaceutical compositions of the present invention are usually prepared following conventional methods and are administered in a pharmaceutically suitable form. For instance, solutions for intravenous injection or infusion may contain as a carrier, for example, sterile water or preferably, they may be in the form of sterile aqueous isotonic saline solutions.

Suspensions or solutions for intramuscular injections may contain, together with the active compound a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulation. Said pharmaceutical preparations may be manufactured by known techniques, for example by means of mixing, granulating, tabletting, sugar-coating or filmcoating processes.

Further object of the present invention are, the compounds of formula (I) for use in a method for treating the human or animal body by therapy.

Furthermore, the present invention provides a method for treating tumors in a patient in need of it, which comprises administering to said patient a composition of the invention.

A further object of the present invention is a combined method for treating cancer or for ameliorating the conditions of mammals, including humans, suffering from cancer, said method comprising administering a compound of formula (I), or a pharmaceutically acceptable salt thereof, and an additional antitumor agent, close enough in time and in amounts sufficient to produce a therapeutically useful effect.

The present invention also provides products containing a compound of formula (I), or a pharmaceutically acceptable salt thereof, and an additional antitumour agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Examples of antitumor agents that can be formulated with a compound of formula (I), or alternatively, can be administered in a combined method of treatment, include doxorubicin, daunomycin, epirubicin, idarubicin, etoposide, fluoro-uracil, melphalan, cyclophosphamide, 4-demethoxy daunorubicin, bleomycin, vinblastin, and mitomycin, or mixtures thereof.

The following examples are given to better illustrate the present invention, but do not limit the scope of the invention itself.

EXAMPLE 1

3-[1-Methyl-4[1-methyl-4[1-methyl-4[5(α-bromoacrylamido)benzofurane-2-carboxamido] pyrrole- 2-carboxamido]pyrrole-2-carboxamido] pyrrole-2-carboxamido]propion-N,N'-dimethylamidine Hydrochloride (11)

Step I: The Intermediate 5-α-Bromoacrylamidobenzofurane-2-carboxylic Acid

To a solution of 500 mg of commercial α-bromoacrylic acid in 5 ml of acetonitrile, a solution of 343 mg of N,N-dicyclohexylcarbodiimide in 15 ml of acetonitrile was slowly added. After one hour, the solution obtained after filtration of the precipitate was added to a solution of 294 mg of 5-amino-2-benzofuranic acid, prepared as reported in Helv. Chim. Acta 31, 75 (1948), and 229 mg of sodium bicarbonate in 20 ml of water. The reaction was stirred at room temperature for one hour, then 2N hydrochloric acid was added until pH=4. The solution was extracted with ethyl acetate (3×10 ml), dried over sodium sulfate and evaporated to dryness in vacuo and the crude residue purified by flash chromatography with a methylene chloride/methanol mixture to yield 500 mg of the intermediate as a pale yellow solid.

By analogous procedure and by using the opportune starting materials the following products can be obtained:

5-α-bromoacrylamidobenzothiophene-2-carboxylic acid;

5-α-bromoacrylamidoindole-2-carboxylic acid;

1-methyl-5-α-bromoacrylamidoindole-2-carboxylic acid;

5-α-bromoacrylamidoindazole-2-carboxylic acid;

1-methyl-5-α-bromoacrylamidoindazole-2-carboxylic acid;

5-α-chloroacrylamidoindole-2-carboxylic acid;

1-methyl-5-α-chloroacrylamidoindole-2-carboxylic acid.

Step II: The Title Compound

A solution of 250 mg of N-deformyldistamycin A N,N'-dimethyl dihydrochloride, prepared as reported in WO 97/28123, in 5 ml of dry DMF was cooled to 5° C. and added with 0.086 ml of N,N'-diisopropylethylamine. After 10 min, 180 mg of the intermediate obtained from step I, and 192 mg of N-ethyl-N'-(3-dimethylaminopropyl)carbodiimide (EDCI) were added. The reaction was stirred at room temperature for 16 hours, then 2N hydrochloric acid was added until pH=4. The solvent was evaporated in vacuo and the crude residue purified by flash chromatography (methylene chloride/methanol:8/2) to yield a yellow oil which was precipitated from methanol/diethyl ether obtaining 200 mg of the title compound as a pale yellow solid.

FAB-MS: m/z, 775(100, [M+H]$^+$); PMR (DMSO-$d_6$) δ: 10.69 (s, 1H), 10.39 (s, 1H), 10.00 (s, 1H), 9.91 (s, 1H), 9.41 (q, J=5.1 Hz, 1H), 8.66 (q, J=4.8 Hz, 1H), 8.27 (t, J=5.7 Hz, 1H), 8.14 (s, 1H); 7.66 (m, 3H), 7.32 (d, J=1.7 Hz, 1H), 7.24 (d, J=1.7 Hz, 1H), 7.18 (d, J=1.7 Hz, 1H), 7.15 (d, J=1.7 Hz, 1H), 7.07 (d, J=1.7 Hz, 1H), 6.93 (d, J=1.7 Hz, 1H), 6.78 (d, J=3.0 Hz, 1H), 6.31 (d, J=3.0 Hz, 1H), 3.87 (s, 3H), 3.84 (s, 3H), 3.80 (s, 3H), 3.00 (d, J=4.8 Hz, 3H), 2.77 (d, J=5.1 Hz, 3H), 2.71 (t, J=6.3 Hz, 2H).

By analogous procedure and by using the opportune starting materials the following products can be obtained:

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propioncyanamidine (1);

3-[1-methyl-4[1-methyl-4[1-methyl-4[1-methyl-5((α-bromoacrylamido)indazole-2-carboxamido]pyrrole-2-carboxamido]pyrrole-2-carboxamido]pyrrole-2-carboxamido]propioncyanamidine (2);

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propion-N-methylamidine (3)

FAB-MS: m/z, 760(100, [M+H]$^+$); PMR (DMSO-$d_6$) δ: 11.68 (d, J=1.9 Hz, 1H), 10.38 (s, 1H), 10.16 (s, 1H), 10.01 (s, 1H), 9.92 (s, 1H), 9.50 (b.s., 1H), 9.10 (b.s., 1H), 8.55 (b.s., 1H), 8.21 (t, J=5.7 Hz, 1H), 7.99 (s, 1H); 7.39 (m, 2H), 7.34 (d, J=1.7 Hz, 1H), 7.28 (d, J=1.9 Hz, 1H), 7.25 (d, J=1.7 Hz, 1H), 7.18 (d, J=1.7 Hz, 1H), 7.09 (d, J=1.7 Hz, 1H), 7.07 (d, J=1.7 Hz, 1H), 6.94 (d, J=11.7 Hz, 1H), 6.74 (d, J=3.0 Hz, 1H), 6.26 (d, J=3.0 Hz, 1H), 3.88 (s, 3H), 3.84 (s, 3H), 3.80 (s, 3H), 3.49 (m, 2H), 2.80 (d, J=5.0 Hz, 3H), 2.60 (m, 2H);

3-[1-methyl-4[1-methyl-4[1-methyl-4[1-methyl-5(α-bromoacrylamido) indole-2-carboxamido]pyrrole-2-carboxamido]pyrrole-2-carboxamido]pyrrole-2-carboxamido]propion-N-methylamidine (4).

FAB-MS: m/z 774(100, [M+H]$^+$); PMR (DMSO-$d_6$) δ: 10.44 (s, 1H), 10.23 (s, 1H), 10.00 (s, 1H), 9.93 (s, 1H), 9.54 (b.s., 1H), 9.13 (b.s., 1H), 8.57 (b.s., 1H), 8.22 (t, J=5.8 Hz, 1H), 8.04 (d, J=1.7 Hz, 1H), 7.56 (d, J=9.0 Hz, 1H), 7.46 (dd, J=9.0 Hz and 1.7 Hz, 1H), 7.33 (d, J=1.7 Hz, 1H), 7.25 (d, J=1.7 Hz, 1H), 7.20 (s, 1H), 7.19 (d, J=1.7 Hz, 1H), 7.12 (d, J=1.7 Hz, 1H), 7.07 (d, J=1.7 Hz, 1H), 6.93 (d, J=1.7 Hz, 1H), 6.77 (d, J=3.0 Hz, 1H), 6.28 (d, J=3.0 Hz, 1H), 4.01 (s, 3H), 3.87 (s, 3H), 3.84 (s, 3H), 3.80 (s, 3H), 3.48 (m, 2H), 2.78 (d, J=5.0 Hz, 3H), 2.60 (t, J=6.3 Hz, 2H);

3-[1-methyl-4[1-methyl-4[1-methyl-4[1-methyl-5(α-chloroacrylamido)indole-2-carboxamido]pyrrole-2-carboxamido]pyrrole-2-carboxamido]pyrrole-2-carboxamido]propion-N-methylamidine (5);

3-[1-methyl-4[1-methyl-4[1-methyl-4[5(α-bromoacrylamido)benzofurane-2-carboxamido] pyrrole-2-carboxamido]pyrrole-2-carboxamido] pyrrole-2-carboxamido]propion-N-methylamidine (6).

FAB-MS: m/z, 761(100, [M+H]$^+$); PMR (DMSO-$d_6$) δ: 10.69 (s, 1H), 10.39 (s, 1H), 10.00 (s, 1H), 9.90 (s, 1H), 9.50 (b.s., 1H), 9.10 (s, 1H), 8.55 (s, 1H), 8.20 (t, J=5.7 Hz, 1H), 8.14 (s, 1H), 7.65 (m, 3H), 7.32 (d, J=1.7 Hz, 1H), 7.23 (d, J=1.7 Hz, 1H), 7.17 (d, J=1.7 Hz, 1H), 7.15 (d, J=1.7 Hz,

1H), 7.07 (d, J=1.7 Hz, 1H), 6.93 (d, J=1.7 Hz, 1H), 6.78 (d, J=3.0 Hz, 1H), 6.29 (d, J=3.0 Hz, 1H), 3.87 (s, 3H), 3.84 (s, 3H), 3.80 (s, 3H), 3.49 (m, 2H), 2.79 (d, J=5.1 Hz, 3H), 2.59 (t, J=6.4 Hz, 2H);

3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propion-N-methylamidine (7).

FAB-MS: m/z, 777(100, [M+H]$^+$); PMR (DMSO-d$_6$) δ: 10.67 (s, 1H), 10.46 (s, 1H), 10.00 (s, 1H), 9.92 (s, 1H), 9.48 (b.s., 1H), 9.09 (s, 1H), 8.54 (s, 1H), 8,35 (d, J=2.1 Hz, 1H), 8.23 (s, 1H), 8.21 (t, J=5.9 Hz, 1H), 7.99 (d, J=9.0 Hz, 1H), 7.66 (dd, J=9.0 and 2.1 Hz, 1H), 7.31 (d, J=1.7 Hz, 1H), 7.24 (d, J=1.7 Hz, 1H), 7.18 (di J=1.7 Hz, 1H), 7.11 (d, J=1.7 Hz, 1H), 7.06 (d, J=1.7 Hz, 1H), 6.93 (d J=1.7 Hz, 1H), 6.80 (d, J=3.0 Hz, 1H), 6.34 (d, J=3.0 Hz, 1H), 3.87 (s, 3H), 3.84 (s, 3H), 3.79 (s, 3H), 3.48 (m, 2H), 2.78 (d, J=5.1 Hz, 3H), 2.58 (t, J=6.4 Hz, 2H);

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propion-N,N'-dimethylamidine (8).

FAB-MS: m/z, 774(100, [M+H]$^+$); PMR (DMSO-d$_6$) δ: 11.68 (d, J=2.0 Hz, 1H), 10.39 (s, 1H), 10.15 (s, 1H), 9.99 (s, 1H), 9.92 (s, 1H), 9.48 (q, J=4.7 Hz, 1H), 8.73 (q, J=4.7 Hz, 1H), 7.99 (s, 1H), 7.34 (d, J=1.7 Hz, 1H), 7.28 (d, J=2.0 Hz, 1H), 7.25 (d, J=1.7 Hz, 1H), 7.19 (d, J=1.7 Hz, 1H), 7.09 (d, J=1.7 Hz, 1H), 7.07 (d, J=1.7 Hz, 1H), 6.93 (d, J=1.7 Hz, 1H), 6.74 (d, J=3.0 Hz, 1H), 6.26 (d, J=3.0 Hz, 1H), 3.88 (s, 3H), 3.84 (s, 3H),3.80 (s, 3H), 3.45 (m, 2H), 3.00 (d, J=4.7 Hz, 3H), 2.78 (t, J=4.7 Hz, 2H);

3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propion-N,N'-dimethylamidine (9);

3-[1-methyl-4[1-methyl-4[1-methyl-4[1-methyl-5(α-bromoacrylamido) indole-2-carboxamido]pyrrole-2-carboxamido]pyrrole-2-carboxamido]pyrrole-2-carboxamido]propion-N,N'-dimethylamidine (10)

FAB-MS: m/z, 788(100, ([M+H]$^+$); PMR (DMSO-d$_6$) δ: 10.43 (s, 1H), 10.22 (s, 1H), 10.00 (s, 1H), 9.93 (s, 1H), 9.46 (q, J=4.7 Hz, 1H), 8.70 (q, J=5.0 Hz, 1H), 8.30 (t, J=5.7 Hz, 2H), 8.04 (d, J=1.9 Hz, 1H), 7.54 (d, J=9.2 Hz, 1H), 7.46 (dd, J=9.2 and 1.9 Hz, 1H), 7.20 (s, 1H), 7.33 (d, J=1.7 Hz, 1H), 7.25 (d, J=1.7 Hz, 1H), 7.19 (d, J=1.7 Hz, 1H), 7.12 (d, J=1.7 Hz, 1H), 7.07 (d, J=1.7 Hz, 1H), 6.93 (d, J=1.7 Hz, 1H), 6.76 (d, J=3.0 Hz, 1H), 6.28 (d, J=3.0 Hz, 1H), 4.01 (s, 3H), 3.87 (s, 3H), 3.84 (s, 3H), 3.80 (s, 3H), 3.45 (m, 2H), 3.00 (d, J=4.7 Hz, 3H), 2.79 (d, J=5.0 Hz, 2H), 2.70 (t, J=6.3 Hz, 2H);

3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propion-N,N'-dimethylamidine (12).

FAB-MS: m/z, 789(100, [M+H]$^+$); PMR (DMSO-d$_6$) δ: 10.64 (s, 1H), 10.44 (s, 1H), 10.98 (s, 1H), 9.91 (s, 1H), 9.38 (q, J=4.8 Hz, 1H), 8.63 (q, J=4.6 Hz, 1H), 8.35 (t, J=2.0 Hz, 1H), 8.26 (t, J=5.7 Hz, 1H), 8.21 (s, 1H), 7.98 (d, J=8.8 Hz, 1H), 7.65 (dd, J=8.8 and 2.0 Hz, 1H), 7.31 (d, J=1.7 Hz, 1H), 7.24 (d, J=1.7 Hz, 1H), 7.18 (d, J=1.7 Hz, 1H), 7.11 (d, J=1.7 Hz, 1H), 7.07 (d, J=1.7 Hz, 1H), 6.93 (d, J=1.7 Hz, 1H), 6.79 (d, J=3.0 Hz, 1H), 6.33 (d, J=3.0 Hz, 1H), 3.88 (s, 3H), 3.84 (s, 3H), 3.80 (s, 3H), 3.47 (m, 2H), 3.00 (d, J=4.6 Hz, 3H), 2.77 (d, J=4.8 Hz, 3H), 2.71 (m, 2H);

3-[1-methyl-4[1-methyl-4[1-methyl-4[1-methyl-5(α-bromoacrylamido)indazole-2-carboxamido]pyrrole-2-carboxamido]pyrrole-2-carboxamido]pyrrole-2-carboxamido]propion-N,N'-dimethylamidine (13);

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamidoxime (14);

3-[1-methyl-4[1-methyl-4[1-methyl-4[5(α-bromoacrylamido)indazole-2-carboxamido]pyrrole-2-carboxamido]pyrrole-2-carboxamido]pyrrole-2-carboxamido]propionamidoxime (15);

3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propionamide (16);

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamide (17);

3-[1-methyl-4[1-methyl-4[1-methyl-4[5(α-bromoacrylamido) benzofurane-2-carboxamido]pyrrole-2-carboxamido]pyrrole-2-carboxamido]pyrrole-2-carboxamido]propionamide (18);

3-[1-methyl-4[1-methyl-4[1-methyl-4[1-methyl-5(α-chloroacrylamido)indazole-2-carboxamido]pyrrole-2-carboxamido]pyrrole-2-carboxamido]pyrrole-2-carboxamido]propionamide (19);

3-[1-methyl-4[1-methyl-4[1-methyl-4[5-N,N-bis(2-chloroethyl)aminobenzothiophene-2-carboxamido]pyrrole-2-carboxamido]pyrrole-2-carboxamido]pyrrole-2-carboxamido]propionamide (29);

3-[1-methyl-4[1-methyl-4[1-methyl-4[5-N,N-bis(2-chloroethyl)aminobenzofurane-2-carboxamido]pyrrole-2-carboxamido]pyrrole-2-carboxamido]pyrrole-2-carboxamido]propioncyanamidine (24).

EXAMPLE 2

3-[1-Methyl-4[1-methyl-4[1-methyl-4[1-methyl-5 (α-bromoacrylamido)indole-2-carboxamido]pyrrole-2-carboxamido]pyrrole-2-carboxamido]pyrrole-2-carboxamido]propionitrile (23)

Step 1: The Intermediate 3-[1-Methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamidine Hydrochloride.

A solution of 260 mg of N-deformyldistamycin A dihydrochloride, prepared as reported in J. Med. Chem. 32, 774–778 (1989), in 5 ml of dry dimethylformamide (DMF) was cooled to 5° C. and added with 0.086 ml of N,N'-diisopropylethylamine. After 10 min, 180 mg of 5-α-bromoacrylamidoindole-2-carboxylic acid and 190 mg of N-ethyl-N'-(3-dimethylaminopropyl) carbodiimide (EDCI) were added. The reaction was stirred at room temperature for 10 hours, then 2N hydrochloric acid was added up to pH=4. The solvent was removed under reduced pressure and the crude residue purified by flash chromatography (methylene chloride/methanol:8/2) to give 240 mg of the title compound.

FAB-MS: m/z 760, (100, [M+H]$^+$); PMR (DMSO-d$_6$) δ: 10.44 (s, 1H), 10.23 (s, 1H), 10.00 (s, 1H), 9.93 (s, 1H), 8.97 (b.s., 2H), 8.60 (b.s., 2H), 8.22 (t, J=5.7 Hz, 1H), 8.05 (d, J=1.8 Hz, 1H), 7.54 (d, J=8.9 Hz, 1H), 7.47 (dd, J=8.9 Hz and J=1.9 Hz, 1H), 7.25 (d, J=1.8 Hz, 1H), 7.21 (s, 1H), 7.19 (d, J=1.8 Hz, 1H), 7.12 (d, J=1.8 Hz, 1H), 7.07 (d, J=1.8 Hz, 1H), 7.05 (d, J=1.8 Hz, 1H), 6.95 (d, J=1.8 Hz, 1H), 6.77 (d, J=3.1 Hz, 1H), 6.29 (d, J=3.1 Hz, 1H), 4.01 (s, 3H), 3.88 (s, 3H), 3.85 (s, 3H), 3.81 (s, 3H), 3.50 (m, 2H), 2.61 (m, 2H).

Step II: The Title Compound

To a solution of 150 mg of 3-[1-methyl-4[1-methyl-4[1-methyl-4[1-methyl-5(α-bromoacrylamido) indole-2-carboxamido]pyrrole-2-carboxamido]pyrrole-2-carboxamido]pyrrole-2-carboxamido]propionamidine hydrochloride, prepared as described in step I as above, in 10 ml DMF were added 25 mg of potassium carbonate and 20 mg of succinic anhydride. The mixture was heated at 60° C. for 4 hours. The solvent evaporated under vacuum and the crude residue purified by flash chromatography (methylene chloride/methanol:8/2) to yield 100 mg of the title compound as a yellow powder.

FAB-MS: m/z, 741(8, [M+H]$^+$); PMR(DMSO-d$_6$) δ: 10.44 (s, 1H), 10.22 (s, 1H), 10.00 (s, 1H), 9;93 (s, 1H), 8.22 (t, J=5.8 Hz, 1H), 8.04 (d, J=1.7 Hz, 1H), 7.56 (d, J=9.0 Hz, 1H), 7.46 (dd, J=9.0 Hz and 1.7 Hz, 1H), 7.33 (d, J=1.7 Hz, 1H), 7.25 (d, J=1.7 Hz, 1H), 7.20 (s, 1H), 7.19 (d, J=1.7 Hz, 1H), 7.12 (d, J=1.7 Hz, 1H), 7.07 (d, J=1.7 Hz, 1H), 6.93 (d, J=1.7 Hz, 1H), 6.77 (d, J=3.0 Hz, 1H), 6.28 (d, J=3.0 Hz, 1H), 4.01 (s, 3H), 3.87 (s, 3H), 3.84 (s, 3H), 3.80 (s, 3H), 3.40 (m, 2H), 2.72 (t, J=6.4 Hz, 2H).

By analogous procedures and by using the opportune starting materials the following products can be obtained:

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propionitrile (22);

3-[1-methyl-4[1-methyl-4[1-methyl-4[5-N,N-bis(2-chloroethyl)aminoindazole-2-carboxamido]pyrrole-2-carboxamido]pyrrole-2-carboxamido]pyrrole-2-carboxamido]propionitrile (32).

EXAMPLE 3

3-[1-Methyl-4-[-methyl-4-[1-methyl-4-[5-N,N-bis(2-chloroethyl)aminoindole-2-carboxamido]pyrrole-2-carboxamido]pyrrole-2-carboxamido]pyrrole-2-carboxamido]propionamidoxime (27)

Step I: The Intermediate 5-N,N-bis(2-Chloroethyl) aminoindole-2-carboxylic Acid

To a solution of 200 mg of ethyl 5-aminoindole-2-carboxylate, prepared as reported in J. Am. Chem. Soc. 80, 4621 (1958), in 10 ml of methanol cooled at −10° C., cold ethylene oxide (2.5 ml) was added. The reaction flask was sealed and allowed to reach room temperature overnight. Methanol and excess ethylene oxide were removed by evaporation and the crude residue purified by flash chromatography thus obtaining 230 mg of ethyl 5-N,N-bis(2-hydroxyethyl)aminoindole-2-carboxylate which was cooled in ice and 2 ml of phosphorus oxychloride were added. The solution was heated at 100° C. for one hour, then solvent evaporated under vacuum, the residue dissolved in 7 ml of 23% hydrochloric acid and heated at 100° C. for two hours. The solution was cooled at room temperature, diluted with 30 ml of water and extracted with ethyl acetate (2×50 ml). The organic phases were evaporated in vacuo and the residue purified by flash chromatography using a methylene chloride/methanol mixture, yielding 220 mg of the intermediate.

By analogous procedure and by using the opportune starting materials the following products can be obtained:

5-N,N-bis(2-chloroethyl)aminobenzofurane-2-carboxylic acid;

1-methyl-5-N,N-bis(2-chloroethyl)aminoindole-2-carboxylic acid;

5-N,N-bis(2-chloroethyl)aminobenzothiophene-2-carboxylic acid;

5-N,N-bis(2-chloroethyl)aminoindazole-2-carboxylic acid;

1-methyl-5-N,N-bis(2-chloroethyl)aminoindazole-2-carboxylic acid.

Step II: The Intermediate 3-[1-Methyl-4-[1-methyl-4-[1-methyl-4-aminopyrrole-2-carboxamido]pyrrole-2-carboxamido]pyrrole-2-carboxamido]propionamidoxime Hydrochloride 1.2 g of 3-[1-methyl-4-[1-methyl-4-[1-metyhyl-4-nitropyrrole-2-carboxamido]pyrrole-2-carboxamido]pyrrole-2-carboxamido]propionitrile, prepared as reported in J. Med. Chem 22,1296–1301, (1979), was suspended in dry ethanol and the solution saturated with dry hydrogen chloride. After 24 hours at room temperature, the solvent was evaporated under vacuo and the residue treated with two equivalents of solution of hydroxylamine in dry ethanol. After 24 hours at room temperature, the solvent was evaporated in vacuo and the residue purified by flash chromatography yielding 500 mg of 3-[1-methyl-4-[1-methyl-4-[1-methyl-4-nitropyrrole-2-carboxamido]pyrrole-2-carboxamido]pyrrole-2-carboxamido]propionamidoxime which was dissolved in a mixture of methanol-dioxane-10% hydrochloric acid (4:1:1) and reduced over Pd catalyst (10% on charcoal) under hydrogen atmosphere (50 psi) in a Parr apparatus.

The solution obtained after filtration of the catalyst was evaporated in vacuo, and the solid residue suspended in dry ethanol, and filtered to yield 500 mg of the intermediate.

FAB-MS: m/z 480 (20, [M+H]$^+$); PMR (DMSO-d$_6$) δ: 10.18 (b.s., 6H), 9.98 (s, 1H), 8.32 (t, J=5.7 Hz, 1H), 7.25 (d, J=1.7 Hz, 1H), 7.20 (d, J=1.7 Hz, 1H), 7.16(d, J=1.7 Hz, 1H), 7.12 (d, J=1.7 Hz, 1H), 7.10 (d, J=1.7 Hz, 1H), 6.93 (d, J=1.7 Hz, 1H), 3.89 (s, 3H), 3.86 (s, 3H), 3.82 (b.s., 7H), 3.50 (m, 2H), 2.72 (m, 2H).

By analogous procedure and by using the opportune starting materials the following compounds can be obtained:

3-[1-methyl-4-[1-methyl-4-[1-methyl-4-aminopyrrole-2-carboxamido]pyrrole-2-carboxamido]pyrrole-2-carboxamido]propioncyanamidine hydrochloride;

3-[1-methyl-4-[1-methyl-4-[1-methyl-4-aminopyrrole-2-carboxamido]pyrrole-2-carboxamido]pyrrole-2-carboxamido]propion-N-methylamidine dihydrochloride;

3-[1-methyl-4-[1-methyl-4-[1-methyl-4-aminopyrrole-2-carboxamido]pyrrole-2-carboxamido]pyrrole-2-carboxamido]propion-N,N'-dimethylamidine dihydrochloride.

Step III: The Title Compound

A solution of 210 mg of 5-N,N-bis(2-chloroethyl) aminoindole-2-carboxylic acid, prepared as reported in step I, and 106 mg of 1-hydroxybenzotriazole hydrate in 10 ml of DMF was stirred at 70° C. for four hours, cooled to room temperature and then added with 310 mg of the intermediate obtained from step I and 118 mg of potassium bicarbonate in 20 ml of water.

The mixture was stirred at room temperature for 3 hours, the solvent was evaporated in vacuo and the crude residue purified by flash chromatography (methylene chloride/methanol: 8/2) to yield 180 mg of the title compound as a yellow solid.

FAB-MS: m/z 752 (20, [M+H]$^+$); PMR (DMSO-d$_6$) δ: 11.35 (d, J=1.8 Hz, 1H), 10.29 (s, 1H), 9.96 (s, 1H), 9.89 (s, 1H), 9.10 (b.s., 1H), 8.18 (t, J=5.6 Hz, 1H), 7.30 (m, 2H), 7.10 (d, J=1.8 Hz, 1H), 7.20 (d, J=1.8 Hz, 1H), 7.14 (d, J=1.8

Hz, 1H), 7.04 (d, J=1.8 Hz, 1H), 7.02 (d, J=1.8 Hz, 1H), 6.92 (d, J=1.8 Hz, 1H), 6.91 (d, J=1.8 Hz, 1H), 6.84 (dd, J=2.3 Hz and J=9.0 Hz, 1H), 5.40 (b.s., 2H), 3.84 (s, 3H), 3.80 (s, 3H), 3.76 (s, 3H), 3.66 (m, 8H), 3.01 (m, 2H), 2.00 (m, 2H).

By analogous procedure and by using the opportune starting materials the following products can be obtained:

3-[1-methyl-4[1-methyl-4[1-methyl-4[5-N,N-bis(2-chloroethyl) aminobenzofurane-2-carboxamido]pyrrole-2-carboxamido]pyrrole-2-carboxamido]pyrrole-2-carboxamido]propioncyanamidine (24);

3-[1-methyl-4[1-methyl-4[1-methyl-4[5-N,N-bis(2-chloroethyl)aminoindazole-2-carboxamido]pyrrole-2-carboxamido]pyrrole-2-carboxamido]pyrrole-2-carboxamido]propion-N-methylamidine (25);

3-[1-methyl-4[1-methyl-4[1-methyl-4[1-methyl-5-N,N-bis(2-chloroethyl)aminoindazole-2-carboxamido]pyrrole-2-carboxamido]pyrrole-2-carboxamido]pyrrole-2-carboxamido]propion-N,N'-dimethylamidine (26);

3-[1-methyl-4[1-methyl-4[1-methyl-4[5-N,N-bis(2-chloroethyl)aminobenzofurane-2-carboxamido]pyrrole-2-carboxamido]pyrrole-2-carboxamido]pyrrole-2-carboxamido]propionamidoxime (28).

EXAMPLE 4

2-[1-Methyl-4[1-methyl-4[1-methyl-4[5-N,N-bis(2-chloroethyl)aminobenzofurane-2-carboxamido]pyrrole-2-carboxamido]pyrrole-2-carboxamido]pyrrole-2-carboxamido]ethylguanidine (21)

Step I: The Intermediate 2-Aminoethylguanidine Dihydrochloride

A solution of commercial N-BOC-ethylendiamine (1 g) in dry ethanol (100 ml) and 2-methyl-2-thiopseudourea hydroiodide (1.5 g) was refluxed for 8 hours. The solvent was removed at reduced pressure and the crude residue purified by flash chromatography (methylene chloride/methanol:9/1) to yield 1.5 g of N-BOC-2-aminoethylguanidine hydroiodide as a yellow oil which was dissolved in methanolic hydrochloric acid solution 5N (20 ml) and stirred at room temperature for 3 hours. The white precipitate was collected and washed with dry ethanol, affording 700 mg of the intermediate.

FAB-MS: m/z 103(20, [M+H]$^+$); PMR (DMSO-d$_6$) δ: 8.38 (b.s., 3H), 7.97 (t, J=6 Hz, 1H), 7.51 (b.s., 4H), 3.45 (m, 2H), 2.92 (m, 2H).

Step II: The Intermediate 2-[1-Methyl-4[1-methyl-4[1-methyl-4-aminopyrrole-2-carboxamido]pyrrole-2-carboxamido]pyrrole-2-carboxamido]ethylguanidine Dihydrochloride A solution of 1-methyl-4-[1-methyl-4-[1-methyl-4-nitropyrrole-2-carboxamido]pyrrole-2-carboxamido]pyrrole-2-carboxylic acid (590 mg), prepared as reported in Tetrahedron 34, 2389–2391, (1978), in 20 ml of DMF, 2-aminoethylguanidine dihydrochloride (500 mg), 1-hydroxybenzotriazole hydrate (350 mg), dicycloexylcarbodiimide (880 mg), and sodium bicarbonate (385 mg) was stirred at 70° C. for 4 hours. The solution obtained after filtration was evaporated in vacuo and the residue purified by flash chromatography (methylene chloride/methanol:8/2) to yield 800 mg of 2-[1-methyl-4-[1-methyl-4-[1-methyl-4-nitropyrrole-2-carboxamido]pyrrole-2-carboxamido]pyrrole-2-carboxamido]ethylguanidine hydrochloride, which was dissolved in methanol (100 ml), added with 1N hydrochloric acid solution (2 ml) and reduced over Pd catalyst (10% on charcoal) under hydrogen atmosphere (50 psi) in a Parr apparatus. The solution obtained after filtration of the catalyst was evaporated in vacuo and the solid residue washed with dry ethanol to yield 750 mg of the intermediate as a brown powder.

FAB-MS: m/z 469(15, [M+H]$^+$); PMR (DMSO-d$_6$) δ: 10.38–10.11 (b.s., 4H), 9.98 (s, 1H), 8.28 (b.s., 1H), 8.19 (d, J=1.7 Hz, 1H), 7.73, (b.s., 1H), 7.63 (d, J=1.7 Hz, 1H), 7.60–7.00 (b.s., 4H), 7.28 (d, J=1.7 Hz, 1H), 7.20 (d, J=1.7 Hz, 1H), 7.1 (d, J=1.7 Hz, 1H), 6.92 (d, J=1.7 Hz, 1H), 3.93 (s, 3H), 3.90 (s, 3H), 3.82 (s, 3H), 3.28 (m, 4H).

By analogous procedures and by using the opportune starting materials the following compounds can be obtained:

3-[1-methyl-4-[1-methyl-4-[1-methyl-4-aminopyrrole-2-carboxamido]pyrrole-2-carboxamido]pyrrole-2-carboxamido]propioncyanamidine hydrochloride;

3-[1-methyl-4-[1-methyl-4-[1-methyl-4-aminopyrrole-2-carboxamido]pyrrole-2-carboxamido]pyrrole-2-carboxamido]propion-N-methylamidine dihydrochloride;

3-[1-methyl-4-[1-methyl-4-[1-methyl-4-aminopyrrole-2-carboxamido]pyrrole-2-carboxamido]pyrrole-2-carboxamido]propion-N,N'-dimethylamidine dihydrochloride;

3-[1-methyl-4[1-methyl-4[1-methyl-4-aminopyrrole-2-carboxamido]pyrrole-2-carboxamido]pyrrole-2-carboxamido]propionamidoxime hydrochloride;

3-[1-methyl-4[1-methyl-4[1-methyl-4-aminopyrrole-2-carboxamido]pyrrole-2-carboxamido]pyrrole-2-carboxamido]propionamide hydrochloride;

3-[1-methyl-4[1-methyl-4[1-methyl-4-aminopyrrole-2-carboxamido]pyrrole-2-carboxamido]pyrrole-2-carboxamido]propionitrile hydrochloride.

Step III: The Intermediate 2-[1-Methyl-[1-methyl-4[1-methyl-4[4-nitrobenzofurane-2-carboxamido]pyrrole-2-carboxamido]pyrrole-2-carboxamido]pyrrole-2-carboxamido]ethylguanidine Dihydrochloride To a solution of 156 mg of 4-nitrobenzofurane-2-carboxylic acid, prepared as reported in Synth. Commun. 21, 959, (1991), in 10 ml of benzene, 0.5 ml of thionyl chloride were added. The mixture was refluxed for two hours, the solvent evaporated under vacuum, the crude solid residue dissolved in 15 ml of dioxane and added portionwise to a solution of 220 mg of the intermediate obtained from step II and 95 mg of sodium bicarbonate in 10 ml of water. The mixture was stirred for one hour and then added of 2N hydrochloric acid until pH=4. The solvent was evaporated in vacuo and the residue purified by flash chromatography chromatography with a mixture methylene chloride/methanol to yield 230 mg of the title compound as a solid.

By analogous procedure and by using the opportune starting materials the following products can be obtained:

3-[1-methyl-[1-methyl-4[1-methyl-4[4-nitrobenzofurane-2-carboxamido]pyrrole-2-carboxamido]pyrrole-2-carboxamido]pyrrole-2-carboxamido]propion-N-methylamidine dihydrochloride;

3-[1-methyl-[1-methyl-4[1-methyl-4[4-nitroindole-2-carboxamido]pyrrole-2-carboxamido]pyrrole-2-carboxamido]pyrrole-2-carboxamido]propioncyanamidine hydrochloride;

3-[1-methyl-4[1-methyl-4[4-nitroindole-2-carboxamido]pyrrole-2-carboxamido]pyrrole-2-carboxamido]propionamidine dihydrochloride;

3-[1-methyl-[1-methyl-4[1-methyl-4[1-methyl-4-nitroindole-2-carboxamido]pyrrole-2-carboxamido]pyrrole-2-carboxamido]pyrrole-2-carboxamido]propion-N,N'didethylamidine dihydrochloride;

3-[1-methyl-[1-methyl-4[1-methyl-4-nitroindole-2-carboxamido]pyrrole-2-carboxamido]pyrrole-2-carboxamido]propionamidoxime hydrochloride;

3-[1-methyl-[1-methyl-4[1-methyl-4[4-nitroindazole-2-carboxamido]pyrrole-2-carboxamido]pyrrole-2-carboxamido]pyrrole-2-carboxamido]propionamide hydrochloride;

3-[1-methyl-[1-methyl-4[4-nitroindazole-2-carboxamido]pyrrole-2-carboxamido]pyrrole-2-carboxamido]propionitrile hydrochloride;

3-[1-methyl-[1-methyl-4[1-methyl-4[1-methyl-4-nitroindazole-2-carboxamido]pyrrole-2-carboxamido]pyrrole-2-carboxamido]pyrrole-2-carboxamido]propionamide dihydrochloride.

Step IV: The Title Compound

The derivative (220 mg) obtained from Step I was dissolved in 10 ml of DMF and reduced over Pd catalyst (10% on charcoal) under reduced pressure (50 psi) in a Parr apparatus. The solution obtained after filtration of the catalyst was evaporated in vacuo and the solid residue dissolved in a solution of dioxane (10 ml) and water (3 ml) and added with 110 mg of 2-bromoacryloyl chloride in 5 ml of dioxane. The solution was stirred for 2 hours at room temperature, then 2N hydrochloric acid was added until pH=4. The solvent was evaporated and the crude residue purified by flash chromatography (methylene chloride/methanol:8/2),to give 180 mg of the title compound as a yellow solid.

FAB-MS: m/z, 751(20, [M+H]$^+$); PMR (DMSO-d$_6$) δ: 10.60 (s, 1H), 9.98 (s, 1H), 9.90 (s, 1H), 8.19 (t, J=5.6 Hz, 1H), 7.56 (b.s., 1H), 7.52 (d, J=9.0 Hz, 1H), 7.50 (s, 1H), 7.20 (b.s., 4H), 6.9–7.4 (m, 8H), 3.86 (s, 3H), 3.84 (s, 3H), 3.80 (s, 3H), 3.75 (m, 8H), 3.30 (m, 4H);

By analogous procedure and by using the opportune starting materials the following compounds can be obtained:

2-[1-methyl-4[1-methyl-4[1-methyl-4[1-methyl-5-N,N-bis(2-chloroethyl)aminoindole-2-carboxamido]pyrrole-2-carboxamido]pyrrole-2-carboxamido]pyrrole-2-carboxamido]ethylguanidine (31);

2-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]ethylguanidine (20);

2-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]ethylguanidine (30).

EXAMPLE 5

Tablets each weighing 0.250 g and containing 50 mg of the active compound of formula (I) can be manufactured as follows:

| Composition for 10,000 tablets | |
|---|---|
| 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propion-N-methylamidine hydrochloride | 500 g |
| Lactose | 1,400 g |
| Corn starch | 500 g |
| Talc powder | 80 g |
| Magnesium stearate | 20 g |

The compound of formula (I), lactose and half of the corn starch were mixed and the mixture was then forced through a sieve of 0.5 mm mesh size.

Corn starch (10 g) was suspended in warm water (90 ml) and the resulting paste was used to granulate the powder. The granulate was dried, comminuted on a sieve of 1.4 mm mesh size, then the remaining quantity of starch, talc and magnesium stearate were added, carefully mixed and processed into tablets.

EXAMPLE 6

Capsules, each dosed at 0.200 g and containing 20 mg of the active compound of formula (I) can be prepared as follows:

| Composition for 500 capsules | |
|---|---|
| 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propion-N-methylamidine hydrochloride | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

EXAMPLE 7

Intramuscular Injection 25 mg/ml

An injectable pharmaceutical composition can be manufactured by dissolving 25 g of 3-[1-methyl-4[1-methyl-4[1-methyl-4[1-methyl-5(α-bromoacrylamido) indole-2-carboxamido]pyrrole-2-carboxamido]pyrrole-2-carboxamido]pyrrole-2-carboxamido]propion-N-methylamidine hydrochloride in sterile propyleneglycol (1000 ml) and sealing ampoules of 1,5 ml.

What is claimed is:

1. A compound which is a benzoheterocyclic distamycin derivative of formula:

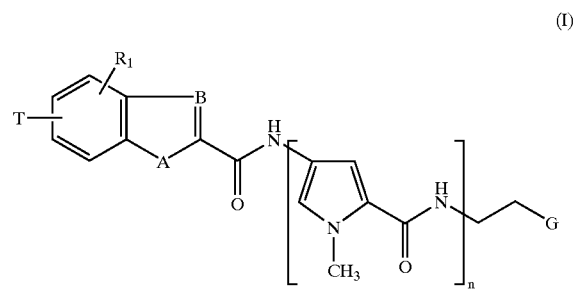

wherein:

n is 2, 3 or 4;

A is a heteroatom selected from O and S or is a group NR, wherein R is hydrogen or C$_1$–C$_4$ alkyl;

B is CH or N;

R$_1$ is hydrogen or C$_1$–C$_4$ alkyl;

G is selected from the group consisting of:

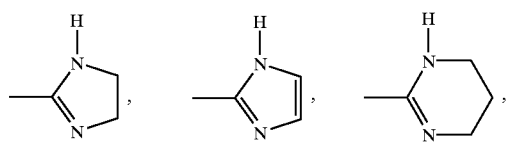

-continued

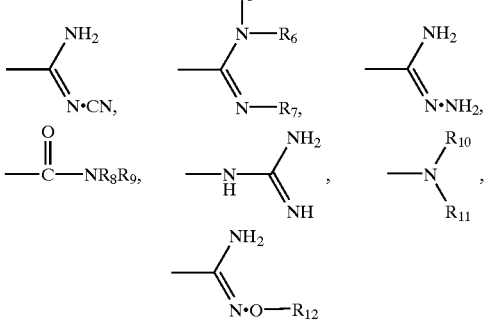

and —C≡N wherein $R_5$, $R_6$, $R_7$, $R_8$, $R_9$, $R_{10}$, $R_{11}$ and $R_{12}$ are, independently from each other, hydrogen or $C_1$–$C_4$ alkyl;

T is a group of formula (II) or (III) as defined below

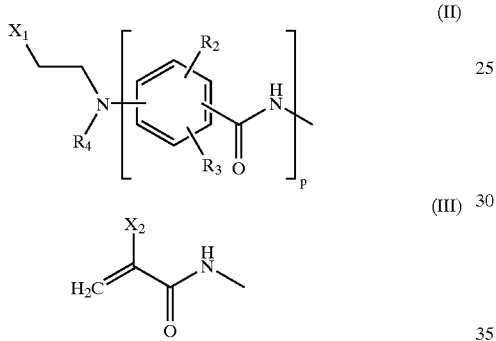

wherein p is 0 or 1; $R_2$ and $R_3$ are, independently from each other, hydrogen, $C_1$–$C_4$ alkyl optionally substituted by one or more fluorine atoms, or $C_1$–$C_4$ alkoxy; $R_4$ is $C_1$–$C_4$ alkyl or $C_1$–$C_3$ haloalkyl; $X_1$ and $X_2$ are halogen atoms;

or a pharmaceutically acceptable salt thereof;

provided that at least one of $R_5$, $R_6$ and $R_7$ is alkyl.

2. A compound according to claim 1 wherein:

B is as defined in claim 1;

n is 2 or 3;

A is O, S, NH or $NCH_3$;

$R_1$ is hydrogen;

G is selected from:

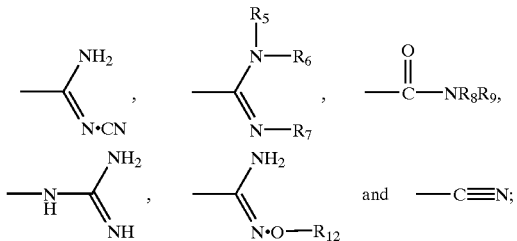

wherein $R_5$, $R_6$, and $R_7$ are, independently from each other, hydrogen or methyl; $R_8$, $R_9$ and $R_{12}$ are hydrogen T is a group of formula (II) as defined in claim 1 wherein p is 0, $X_1$ is a chlorine atom and $R_4$ is 2-chloroethyl, or T is a group of formula (III) as defined in claim 1 wherein $X_2$ is chlorine or bromine.

3. A compound of formula (I) according to claim 1 selected from the group consisting of:

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propioncyanamidine;

3-[1-methyl-4[1-methyl-4[1-methyl-4[1-methyl-5(α-bromoacrylamido)indazole-2-carboxamido]pyrrole-2-carboxamido]pyrrole-2-carboxamido]pyrrole-2-carboxamido]propioncyanamidine;

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propion-N-methylamidine;

3-[1-methyl-4[1-methyl-4[1-methyl-4[1-methyl-5(α-bromoacrylamido)indazole-2-carboxamido]pyrrole-2-carboxamido]pyrrole-2-carboxamido]pyrrole-2-carboxamido]propion-N-methylamidine;

3-[1-methyl-4[1-methyl-4[1-methyl-4[1-methyl-5(α-chloroacrylamido)indole-2-carboxamido]pyrrole-2-carboxamido]pyrrole-2-carboxamido]pyrrole-2-carboxamido]propion-N-methylamidine;

3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propion-N-methylamidine;

3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propion-N-methylamidine;

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propion-N,N'-dimethylamidine;

3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propion-N,N'-dimethylamidine;

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propion-N,N'-dimethylamidine;

3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propion-N,N'-dimethylamidine;

3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propion-N,N'-dimethylamidine;

3-[1-methyl-4[1-methyl-4[1-methyl-4[1-methyl-5(α-bromoacrylamido)indazole-2-carboxamido]pyrrole-2-carboxamido]pyrrole-2-carboxamido]pyrrole-2-carboxamido]propion-N,N'-dimethylamidine;

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamidoxime;

3-[1-methyl-4[1-methyl-4[1-methyl-4[5(α-bromoacrylamido)indazole-2-carboxamido]pyrrole-2-carboxamido]pyrrole-2-carboxamido]pyrrole-2-carboxamido]propionamidoxime;

3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propionamide;

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamide;

3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propionamide;

3-[1-methyl-4[1-methyl-4[1-methyl-4[1-methyl-5(α-chloroacrylamido)indazole-2-carboxamido]pyrrole-2-carboxamido]pyrrole-2-carboxamido]pyrrole-2-carboxamido]propionamide;

2-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]ethylguanidine;

2-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]ethylguanidine;

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propionitrile;

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionitrile;

3-[1-methyl-4[1-methyl-4[1-methyl-4[5-N,N-bis(2-chloroethyl)aminobenzofurane-2-carboxamido]pyrrole-2-carboxamido]pyrrole-2-carboxamido]pyrrole-2-carboxamido]propioncyanamidine;

3-[1-methyl-4[1-methyl-4[1-methyl-4[5-N,N-bis(2-chloroethyl)aminoindazole-2-carboxamido]pyrrole-2-carboxamido]pyrrole-2-carboxamido]pyrrole-2-carboxamido]propion-N-methylamidine;

3-[1-methyl-4[1-methyl-4[1-methyl-4[1-methyl-5-N,N-bis(2-chloroethyl)aminoindazole-2-carboxamido]pyrrole-2-carboxamido]pyrrole-2-carboxamido]pyrrole-2-carboxamido]propion-N,N'-dimethylamidine;

3-[1-methyl-4-[1-methyl-4-[1-methyl-4-[5-N,N-bis(2-chloroethyl)aminoindole-2-carboxamido]pyrrole-2-carboxamido]pyrrole-2-carboxamido]pyrrole-2-carboxamido]propionamidoxime;

3-[1-methyl-4[1-methyl-4[1-methyl-4[5-N,N-bis(2-chloroethyl)aminobenzofurane-2-carboxamido]pyrrole- 2-carboxamido]pyrrole-2-carboxamido]pyrrole-2-carboxamido]propionamidoxime;

3-[1-methyl-4[1-methyl-4[1-methyl-4[5-N,N-bis(2-chloroethyl)aminobenzothiophene-2-carboxamido]pyrrole-2-carboxamido]pyrrole-2-carboxamido]pyrrole-2-carboxamido]propionamide;

2-[1-methyl-4[1-methyl-4[1-methyl-4[5-N,N-bis(2-chloroethyl) aminoindole-2-carboxamido]pyrrole-2-carboxamido]pyrrole-2-carboxamido]pyrrole-2-carboxamido]ethylguanidine;

2-[1-methyl-4[1-methyl-4[1-methyl-4[1-methyl-5-N,N-bis(2-chloroethyl)aminoindole-2-carboxamido]pyrrole-2-carboxamido]pyrrole-2-carboxamido]pyrrole-2-carboxamido]ethylguanidine;

3-[1-methyl-4[1-methyl-4[1-methyl-4[5-N,N-bis(2-chloroethyl)aminoindazole-2-carboxamido]pyrrole-2-carboxamido]pyrrole-2-carboxamido]pyrrole-2-carboxamido]propionitrile; and the pharmaceutically acceptable salts thereof.

4. A process for preparing a compound as defined in claim 1, which process comprises:

(a) reacting a compound of formula:

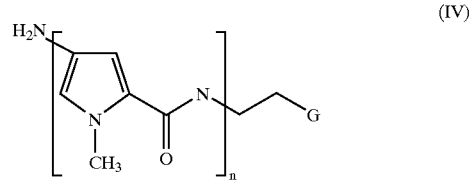

(IV)

wherein n and G are as defined in claim 1 with a compound of formula:

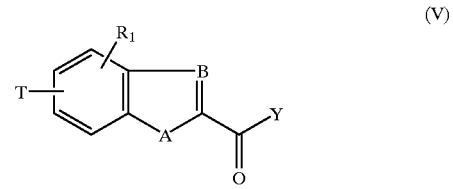

(V)

wherein A, B, T and $R_1$ are as defined in claim 1; is hydroxy or a suitable leaving group; to obtain a compound of formula (I) as defined above; or (b) reacting a compound of formula:

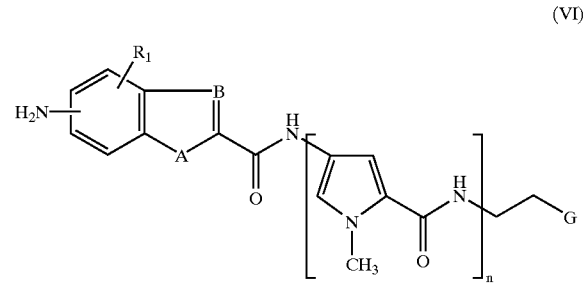

(VI)

wherein n, A, B, G and $R_1$ are as defined above; with a compound of formula:

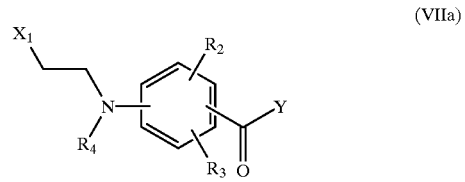

(VIIa)

wherein Y is as defined above; $X_1$, $R_2$, $R_3$ and $R_4$ are as defined in claim 1; or, alternatively, with a compound of formula:

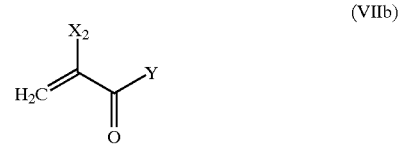

(VIIb)

wherein X₂ is as defined in claim 1; to obtain a compound of formula (I) wherein T is a group of formula (II) with p equal to 1 or a group of formula (III); or (c) reacting a compound of formula (VIII)

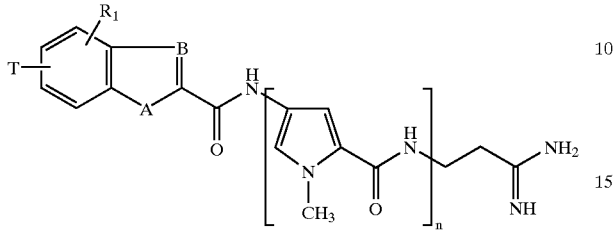

(VIII)

wherein n, A, B, R₁ and T are as defined above; with succinic anhydride, so obtaining a compound of formula (I) having G equal to —C≡N; or (d) reacting a compound of formula (IX):

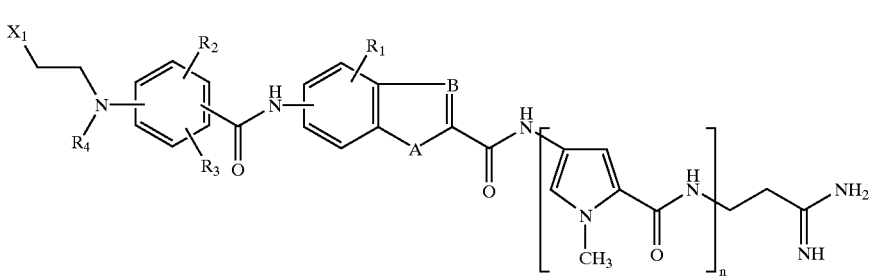

(IX)

wherein n, A, B, R₁, R₂, R₃, R₄ and X₁ are as defined above; with (i) H₂N—(CH₂)ₘ—NH₂, where m is 2 or 3, to obtain a compound of formula (I) wherein G is:

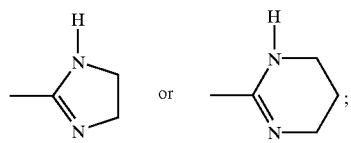

(ii) H₂N—CH₂—CHO to obtain a compound of formula (I) wherein G is:

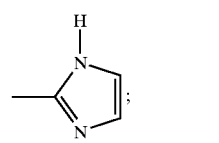

(iii) H₂N—CN, so obtaining a compound of formula (I) having G equal to:

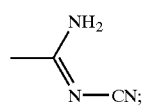

(iv) H₂N—OR₁₂, wherein R₁₂ is as defined above, so obtaining a compound of formula (I) having G equal to:

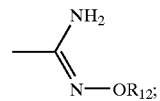

(v) H₂N—NH₂, so obtaining a compound of formula (I) having G equal to:

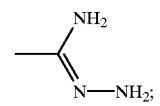

(vi) HNR₅R₆, so obtaining a compound of formula (I) having G equal to:

and then optionally with H₂NR₇, so obtaining a compound of formula (I) having G equal to:

wherein R₅, R₆, and R₇ are, independently from each other, hydrogen or C₁–C₄ alkyl;

(vii) HNR₈R₉, so obtaining a compound of formula (I) having G equal to:

and then with water in an alkaline medium, so obtaining a compound of formula (I) having G equal to —CO—$NR_8R_9$, wherein $R_8$ and $R_9$ are, independently from each other, hydrogen or $C_1$–$C_4$ alkyl; or (viii) water in an alkaline medium, so obtaining a compound of formula (I) having G equal to —$CONH_2$;

and, if desired, (e) converting the compound of formula (I) into a pharmaceutically acceptable salt thereof.

5. A process according to claim 4 wherein Y is selected from the group consisting of chloro, 2,4,5-trichlorophenoxy, 2,4-dinitrophenoxy, succinimido-N-oxy and imidazolyl.

6. A pharmaceutical composition comprising one or more pharmaceutically acceptable carriers and/or diluents and, as the active principle, a compound as defined in claim 1.

7. A method of inhibiting the growth of tumors in mammals which comprises administering the compound of claim 1.

* * * * *